(12) United States Patent
Webster

(10) Patent No.: US 6,210,407 B1
(45) Date of Patent: Apr. 3, 2001

(54) BI-DIRECTIONAL ELECTRODE CATHETER

(75) Inventor: Wilton W. Webster, Diamond Bar, CA (US)

(73) Assignee: Cordis Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/205,631

(22) Filed: Dec. 3, 1998

(51) Int. Cl.[7] .............................. A61B 18/14; A61B 5/042
(52) U.S. Cl. .......................... 606/41; 600/374; 600/393; 604/95; 607/122
(58) Field of Search ................................. 600/374, 393; 607/122; 606/41, 45, 49; 604/95

(56) References Cited

U.S. PATENT DOCUMENTS

| | | |
|---|---|---|
| Re. 34,502 | 1/1994 | Webster, Jr. .......................... 607/125 |
| 3,470,876 | 10/1969 | Barchilon ............................ 128/348 |
| 3,605,725 | 9/1971 | Bentov ............................ 128/2.05 R |
| 3,625,200 | 12/1971 | Muller ............................ 128/2.05 R |
| 4,191,196 | 3/1980 | Bradley et al. ...................... 128/733 |
| 4,203,430 | 5/1980 | Takahashi ................................. 128/4 |
| 4,207,873 | 6/1980 | Kruy ......................................... 128/6 |
| 4,233,991 | 11/1980 | Bradley et al. ...................... 128/733 |
| 4,586,923 | 5/1986 | Gould et al. ........................... 604/95 |
| 4,685,457 | 8/1987 | Donenfeld ....................... 128/207.14 |
| 4,753,223 | 6/1988 | Bremer ................................... 128/4 |
| 4,826,087 | 5/1989 | Chinery ................................ 239/551 |
| 4,838,859 | 6/1989 | Strassman ............................. 604/95 |
| 4,921,482 | 5/1990 | Hammerslag et al. ................ 604/95 |
| 4,960,134 | 10/1990 | Webster, Jr. .......................... 128/786 |
| 4,998,916 | 3/1991 | Hammerslag et al. ................ 604/95 |
| 5,019,090 | 5/1991 | Pinchuk ................................ 606/194 |
| 5,037,391 | 8/1991 | Hammerslag et al. ................ 604/95 |
| 5,108,368 | 4/1992 | Hammerslag et al. ................ 604/95 |
| 5,199,950 | 4/1993 | Schmitt et al. ........................ 604/95 |
| 5,318,525 | 6/1994 | West et al. ............................ 604/95 |
| 5,358,478 | 10/1994 | Thompson et al. ................... 604/95 |
| 5,359,994 | 11/1994 | Krauter et al. .......................... 128/4 |
| 5,364,351 | 11/1994 | Heinzelman et al. ................. 604/95 |
| 5,368,564 | 11/1994 | Savage .................................. 604/95 |
| 5,383,923 | 1/1995 | Webster, Jr. .......................... 607/125 |
| 5,397,304 | 3/1995 | Truckai ................................. 604/95 |
| 5,397,321 | 3/1995 | Houser et al. ........................ 606/41 |
| 5,419,767 | 5/1995 | Eggers et al. ........................ 604/114 |

(List continued on next page.)

*Primary Examiner*—Lee Cohen
(74) *Attorney, Agent, or Firm*—Christie, Parker & Hale, LLP

(57) ABSTRACT

A bi-directional catheter comprises an elongated body, a tip section and a control handle. The body has at least one lumen extending therethrough. The tip section is mounted at the distal end of the catheter body and has at least two diametrically-opposed off-axis lumens. The first off-axis lumen is smaller than the second off-axis lumen. The control handle is mounted at the proximal end of the catheter body and comprises at least two moveable members longitudinally movable between first and second positions. The catheter further comprises first and second puller wires. The proximal end of each puller wire is connected to an associated movable member of the control handle. Each puller wire extends from the control handle through a lumen of the catheter body. The first puller wire extends into the first lumen in the tip section, and the second puller wire extends into the second lumen in the tip section. The distal end of each puller wire is anchored to the tip section. An electrode is mounted on the tip section, and a lead wire is electrically connected to the electrode. The lead wire extends through the second lumen in the tip section, through a lumen in the catheter body and into the control handle. Proximal movement of a movable member relative to the catheter body results in proximal movement of the puller wire associated with that movable member relative to the catheter body, and thus deflection of the tip section in the direction of the lumen in which that puller wire extends.

27 Claims, 8 Drawing Sheets

U.S. PATENT DOCUMENTS

| | | | |
|---|---|---|---|
| 5,431,168 | 7/1995 | Webster, Jr. | 128/658 |
| 5,441,483 | 8/1995 | Avitall | 604/95 |
| 5,456,664 | 10/1995 | Heinzelman et al. | 604/95 |
| 5,492,119 | 2/1996 | Abrams | 128/642 |
| 5,507,725 | 4/1996 | Savage et al. | 604/95 |
| 5,531,686 | 7/1996 | Lundquist et al. | 604/95 |
| 5,582,609 | 12/1996 | Swanson et al. | 606/39 |
| 5,588,964 | 12/1996 | Imran et al. | 604/95 |
| 5,626,136 | 5/1997 | Webster, Jr. | 128/642 |
| 5,656,029 | 8/1997 | Imran et al. | 604/95 |
| 5,656,030 | 8/1997 | Hunjan et al. | 604/95 |
| 5,662,606 | 9/1997 | Cimino et al. | 604/95 |
| 5,681,280 | 10/1997 | Rusk et al. | 604/95 |
| 5,715,817 * | 2/1998 | Stevens-Wright et al. | 606/41 |
| 5,730,704 | 3/1998 | Avitall | 600/374 |
| 5,741,320 | 4/1998 | Thornton et al. | 607/122 |
| 5,807,249 * | 9/1998 | Qin et al. | 606/41 |
| 5,827,272 | 10/1998 | Breining et al. | 606/41 |
| 5,827,278 | 10/1998 | Webster, Jr. | 606/41 |

\* cited by examiner

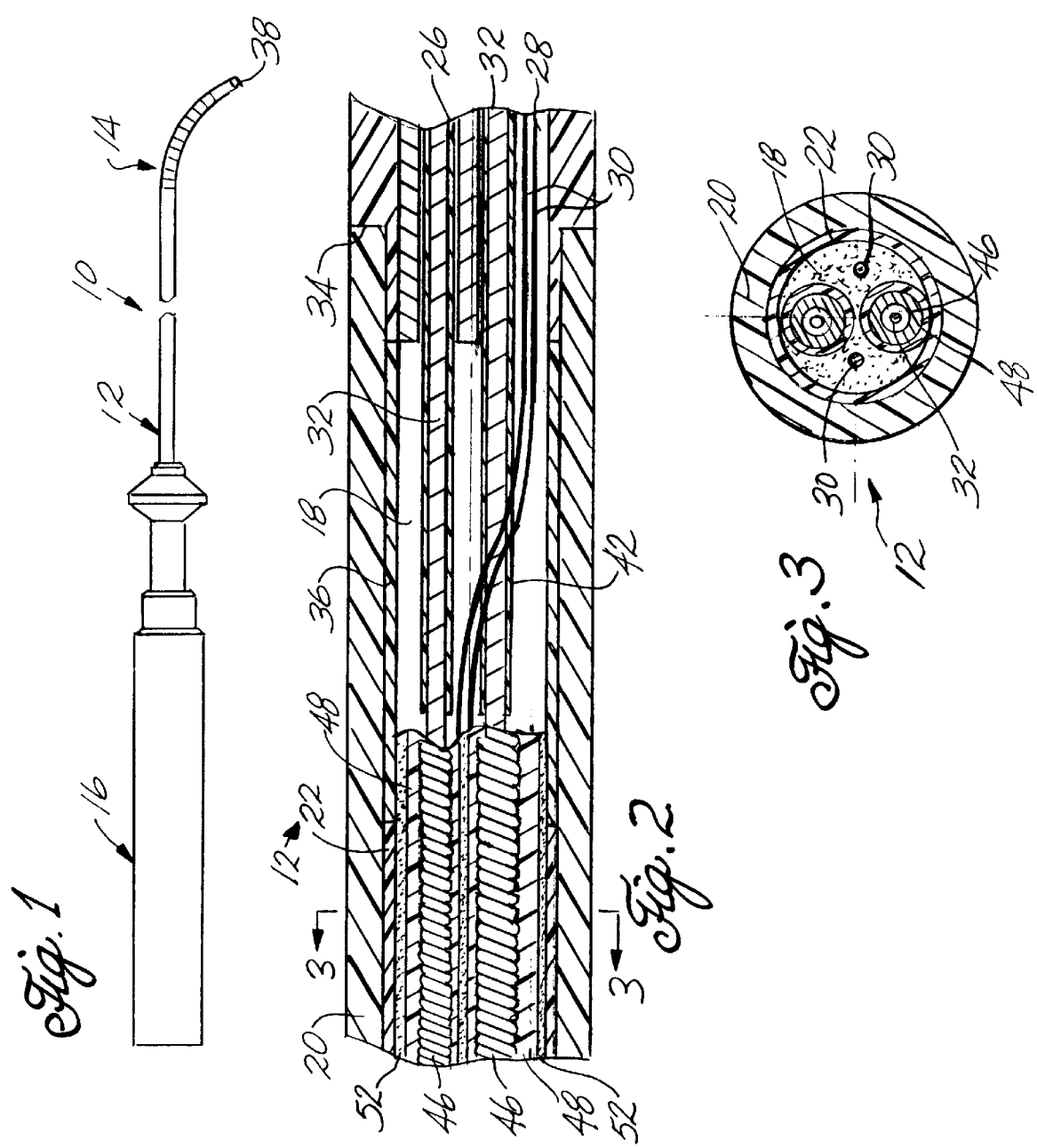

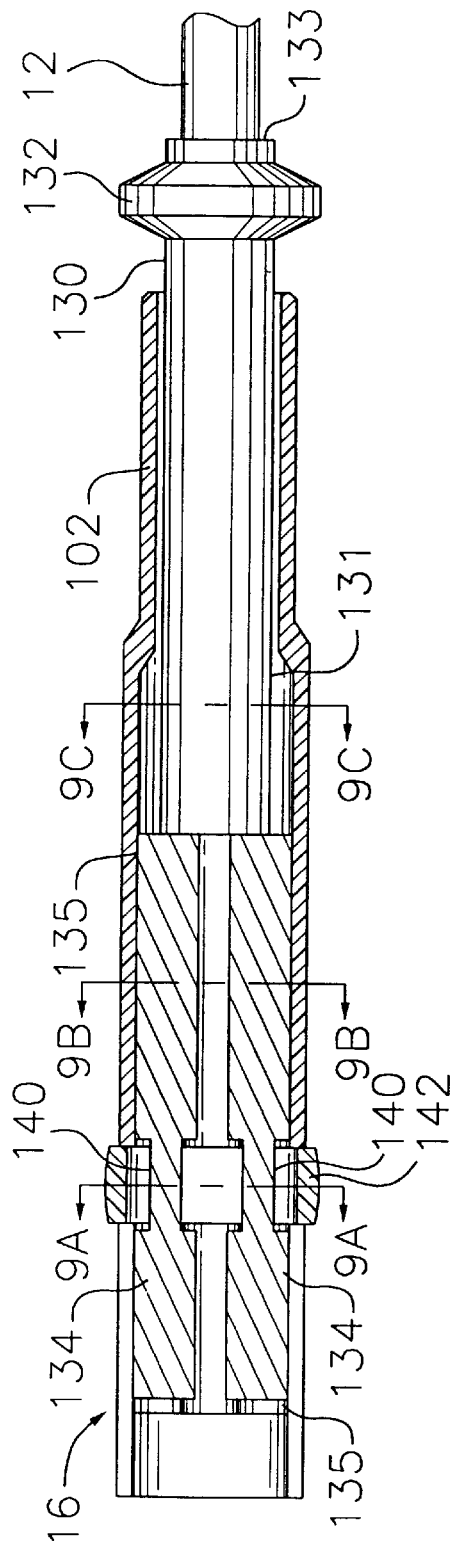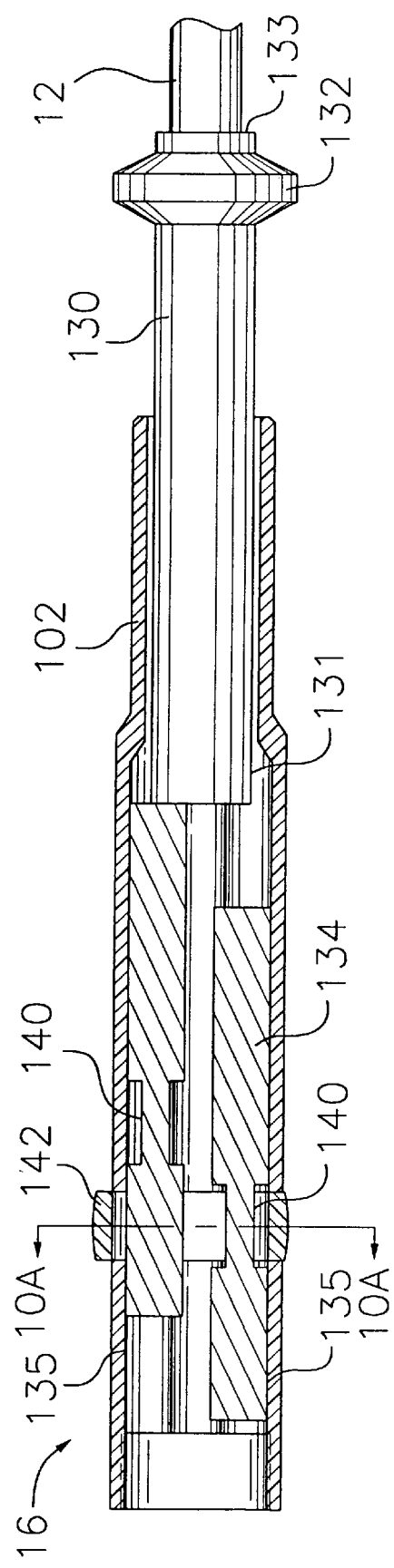

BI-DIRECTIONAL ELECTRODE CATHETER

FIELD OF THE INVENTION

This invention relates to a deflectable catheter, and particularly to an electrode catheter that is deflectable in two directions.

BACKGROUND OF THE INVENTION

Steerable or deflectable tip cardiovascular catheters are useful in many applications, being a marked improvement over catheters with fixed tips. They are especially useful in the field of electrophysiology for performing radiofrequency ablation of cardiac tissue to interrupt abnormal electrical pathways in the heart. Typically, ablation catheters carry one or more electrodes at their distal end. A steerable catheter assists the physician in guiding the distal end of the catheter so that the electrodes can be properly aligned with the tissue to be ablated.

There are presently several useful designs for steerable tip catheters. For example, U.S. Pat. No. RE 34,502, the disclosure of which is incorporated herein by reference, describes a catheter having a control handle comprising a housing having a piston chamber at its distal end. A piston is mounted in the piston chamber and is afforded lengthwise movement. The proximal end of the elongated, tubular catheter body is attached to the piston. A puller wire is attached to the housing and extends through the piston, through the catheter body and into an off-axis lumen in the catheter tip section. The distal end of the puller wire is anchored in the tip section of the catheter. In this arrangement, lengthwise movement of the piston relative to the housing results in deflection of the catheter tip section.

Bidirectional catheters have been designed to be deflectable in one direction by one puller wire and in the opposite direction within the same plane by a second puller wire. In such a construction, the puller wires extend into opposing off-axis lumens within the tip section of the catheter. So that the tip section can bend in both directions in the same plane, the puller wires and their associated lumens must be located along a diameter of the tip section. For ablation catheters, electrode lead wires must also be provided within the distal end. Typically, an additional lumen is used to contain the electrode lead wires. Difficulties have been encountered in designing a distal tip having a relatively small diameter, e.g., 6½ French or less, that contains three lumens where the two puller wire lumens are contained along a diameter. This is especially true where a stainless steel braided tip construction is used and where the braid circumscribes all the lumens.

SUMMARY OF THE INVENTION

The present invention provides a bidirectional electrode catheter which overcomes the drawbacks encountered with small diameter bidirectional catheters. The catheter comprises a pair of off-axis lumens along a diameter for receiving puller wires and wherein the electrode lead wires extend through one of the puller wire lumens. The lumen containing both the lead wire and the puller wire is diametrically opposed to the lumen containing the other puller wire, and preferably has a larger diameter than the other puller wire lumen.

In one embodiment, the invention is directed to a bi-directional catheter comprising an elongated catheter body, a tip section and a control handle. The body has proximal and distal ends and at least one lumen therethrough. The tip section, which is positioned at the distal end of the catheter body, has proximal and distal ends and at least two diametrically-opposed off-axis lumens. The first off-axis lumen is smaller than the second off-axis lumen.

The control handle, which is at the proximal end of the catheter body, comprises at least two moveable members longitudinally movable between first and second positions. First and second puller wires, each having proximal and distal ends, extend within the catheter body. The proximal end of each puller wire is connected to an associated movable member of the control handle. Each puller wire extends from the control handle through a lumen of the catheter body. The first puller wire extends into the first off-axis lumen in the tip section, and the second puller wire extends into the second off-axis lumen in the tip section. The distal end of each puller wire is anchored to the tip section. Proximal movement of one of the movable members relative to the catheter body results in proximal movement of the puller wire associated with that movable member relative to the catheter body, which results in deflection of the tip section in the direction of the lumen in which that puller wire extends.

An electrode is mounted on the tip section, which can be a tip electrode or a ring electrode. Preferably both a tip electrode and at least one ring electrode are mounted on the tip section. A lead wire is provided for each electrode, with the distal end of the lead wire being electrically connected to its associated electrode. Each lead wire extends through the second lumen in the tip section, through a lumen in the catheter body, into the control handle, and to a connector.

DESCRIPTION OF THE DRAWINGS

These and other features of the advantages of the present invention will be better understood by reference to the following detailed description when considered in conjunction with the accompanying drawings wherein:

FIG. 1 is a side view of an embodiment of the catheter of the invention.

FIG. 2 is a side cross-sectional view of the junction of the catheter body and tip section of an embodiment of a catheter according to the invention.

FIG. 3 is a transverse cross-sectional view of the catheter body shown in FIG. 2 taken along line 3—3.

FIG. 9 is a side cross-sectional view of a bidirectional control handle suitable for use in connection with the catheter of the invention.

FIG. 10 is a side cross-sectional view of the bidirectional control handle of FIG. 9 where the piston is extended distally with respect to the handle housing.

DETAILED DESCRIPTION

Figure 5:
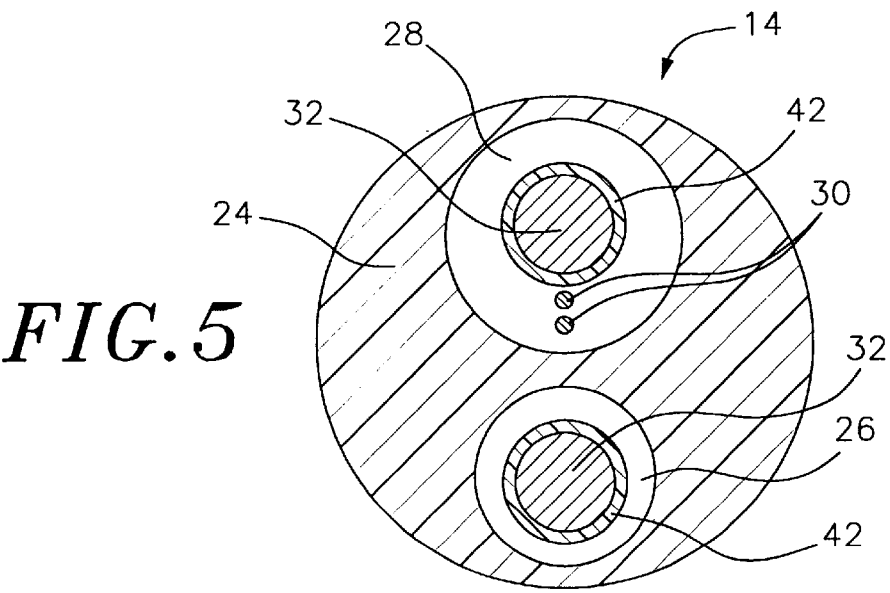
FIG. 5 is a transverse cross-sectional view of the tip section along line 5—5.

In a particularly preferred embodiment of the invention, there is provided a steerable bidirectional electrode catheter. As shown in FIG. 1, the catheter 10 comprises an elongated catheter body 12 having proximal and distal ends, a tip section 14 at the distal end of the catheter body 12, and a control handle 16 at the proximal end of the catheter body 12.

As shown in FIGS. 2 and 3, the catheter body 12 comprises an elongated tubular construction having a single axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 preferably comprises an imbedded braided mesh of stainless steel or the like to increase torsional stiffness of the catheter body 12 so that when the control handle 16 is rotated the tip section 14 will rotate in a corresponding manner.

The overall length and diameter of the catheter 10 may vary according to the application. A presently preferred catheter 10 has an overall length of about 48 inches. The outer diameter of the catheter body 12 is not critical, but is preferably no more than about 8 french. The inner surface of the outer wall 20 is preferably lined with a stiffening tube 22, which can be made of any suitable material, preferably nylon or polyimide, The stiffening tube 22, along with the braided outer wall 20, provides improved flexural and torsional stability while at the same time minimizing the wall thickness of the catheter body 12, thus maximizing the diameter of the central lumen 18. The outer diameter of the stiffening tube 22 is about the same as or slightly smaller than the inner diameter of the outer wall 20. A particularly preferred catheter 10 has an outer diameter of about 0.092 inch and a lumen 18 diameter of about 0.052 inch.

Figure 4:
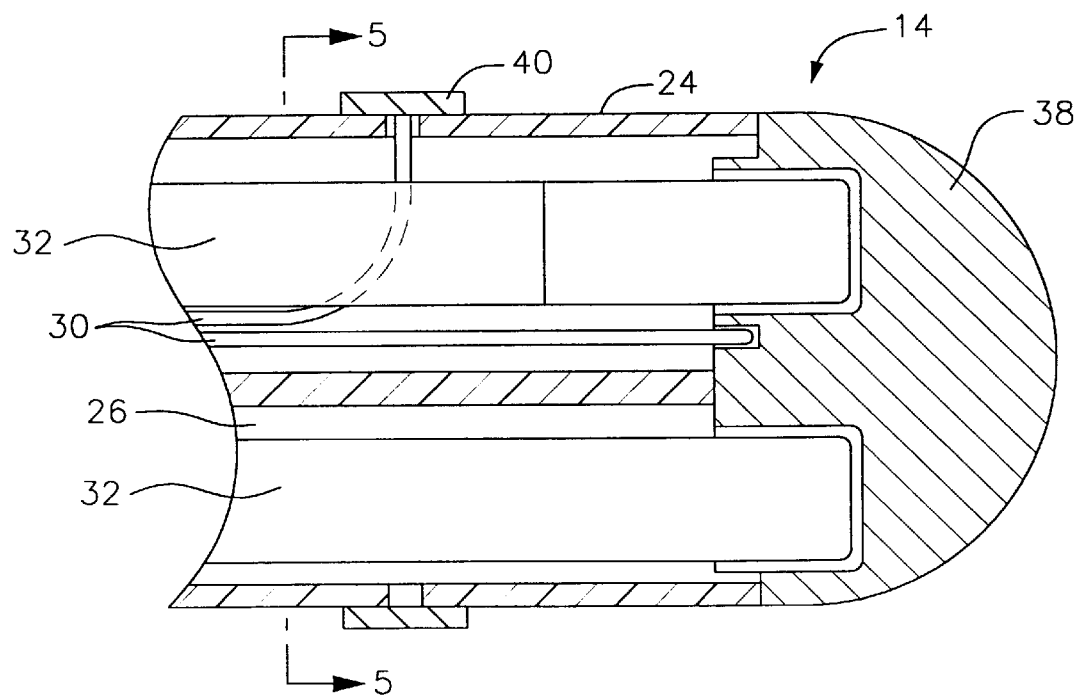
FIG. 4 is a side cross-sectional view of the distal end of the tip section shown in FIG. 2.

As shown in FIGS. 4 and 5, the tip section 14 comprises a short section of flexible tubing 24 having a first off-axis lumen 26 and a second off-axis lumen 28. The flexible tubing 24 is made of a suitable non-toxic material that is preferably more flexible than the catheter body 20. A presently preferred material for the tubing 24 is braided polyurethane, i.e., polyurethane with an embedded mesh of braided stainless steel or the like. The outer diameter of the tip section 14, like that of the catheter body 12, is preferably no greater than about 7 french, more preferably about 6½ french or less.

The off-axis lumens 26, 28 extend through diametrically opposed halves of the tip section 14. The off-axis lumens 26, 28 are asymmetrical and therefore non-interchangeable. The first off-axis lumen 26 is smaller than the second off-axis lumen 28. In an 8 French or 7 French diameter catheter, where the tip section is 6½ French, it is preferred that the first off-axis lumen 26 has a diameter ranging from about 0.018 inch to about 0.025 inch, more preferably from about 0.018 inch to about 0.022 inch. Preferably, the second off-axis lumen 28 has a diameter ranging from about 0.022 inch to about 0.030 inch, more preferably from about 0.026 inch to about 0.028 inch.

By using two rather than three lumens along a single diameter, the present design retains the simplified construction of the unidirectional deflectable steerable catheter described in U.S. Pat. No. Re 34,502, which is incorporated herein by reference.

A preferred means for attaching the catheter body 12 to the tip section 14 is illustrated in FIG. 2. The proximal end of the tip section 14 comprises an outer circumferential notch 34 that receives the inner surface of the outer wall 20 of the catheter body 12. The tip section 14 and catheter body 12 are attached by glue or the like. Before the tip section 14 and catheter body 12 are attached, however, the stiffening tube 22 is inserted into the catheter body 12. The distal end of the stiffening tube 22 is fixedly attached near the distal end of the catheter body 12 by forming a glue joint with polyurethane glue or the like. Preferably a small distance, e.g., about 3 mm, is provided between the distal end of the catheter body 12 and the distal end of the stiffening tube 22 to permit room for the catheter body 12 to receive the notch 34 of the tip section 14. A force is applied to the proximal end of the stiffening tube 22, and, while the stiffening tube 22 is under compression, a first glue joint (not shown) is made between the stiffening tube 22 and the outer wall 20 by a fast drying glue, e.g. Super Glue®. Thereafter a second glue joint is formed between the proximal ends of the stiffening tube 22 and outer wall 20 using a slower drying but stronger glue, e.g., polyurethane.

A spacer 36 lies within the catheter body 12 between the distal end of the stiffening tube 22 and the proximal end of the tip section 14. The spacer 36 is preferably made of a material that is stiffer than the material of the tip section 14, e.g., polyurethane, but not as stiff as the material of the stiffening tube 22, e.g. polyimide. A spacer made of Teflon® is presently preferred. A preferred spacer 36 has a length of from about 0.25 inch to about 0.75 inch, more preferably about 0.50 inch. Preferably the spacer 36 has an outer and inner diameter about the same as the outer and inner diameters of the stiffening tube 22. The spacer 36 provides a transition in flexibility at the junction of the catheter body 12 and the tip section 14 to bend smoothly without folding or kinking.

In the depicted embodiment, the distal end of the tip section 14 carries a tip electrode 38. Mounted along the length of the tip section 14 is a ring electrode 40. (See FIG. 4) The length of the ring electrode 40 is not critical, but is preferably about 1 mm to about 3 mm. Additional ring electrodes can be provided if desired. If multiple ring electrodes are used, they are spaced apart in any fashion as desired so long as their edges do not touch.

The tip electrode 38 and ring electrode 40 are each connected to a separate lead wire 30. Each lead wire 30 extends through the second off-axis lumen 28 in the tip section 14, through the central lumen 18 in the catheter body 12 and through the control handle 16. The proximal end of each lead wire 30 extends out the proximal end of the control handle 16 and is connected to an appropriate connector, which can be plugged into or otherwise connected to a suitable monitor, source of energy, etc.

The lead wires 30 are connected to the tip electrode 38 and ring electrode 40 by any conventional technique. Connection of a lead wire 30 to the tip electrode 38 is preferably accomplished by solder or the like. Connection of a lead wire 30 to a ring electrode 40 is preferably accomplished by first making a small hole through the tubing 24. Such a hole can be created, for example, by inserting a needle through the tubing 24 and heating the needle sufficiently to form a permanent hole. A lead wire 30 is then drawn through the hole by using a microhook or the like. The end of the lead wire 30 is then stripped of any coating and welded to the underside of the ring electrode 40, which is then slid into position over the hole and fixed in place with polyurethane glue or the like.

Two puller wires 32 extend through the catheter 10. Each puller wire 32 extends from the control handle 16, through the central lumen 18 in the catheter body 12 and into one of the off-axis lumens 26 and 28 of the tip section 14. As described in more detail below, the proximal end of each puller wire 32 is anchored within the control handle 16 and the distal end of each puller wire 32 is anchored within the tip section 14.

Each puller wire 32 is made of any suitable metal, such as stainless steel or Nitinol. Preferably each puller wire 32 has a coating, such as a coating of Teflon® or the like. Each puller wire 32 has a diameter preferably ranging from about 0.006 inch to about 0.0010 inch. Preferably both of the puller wires 32 have the same diameter.

Each puller wire 32 is anchored near the distal end of the tip section 14. In the embodiment depicted in FIG. 4, the puller wires 32 are both anchored to the tip electrode 38 by a welding or the like.

Figure 6:
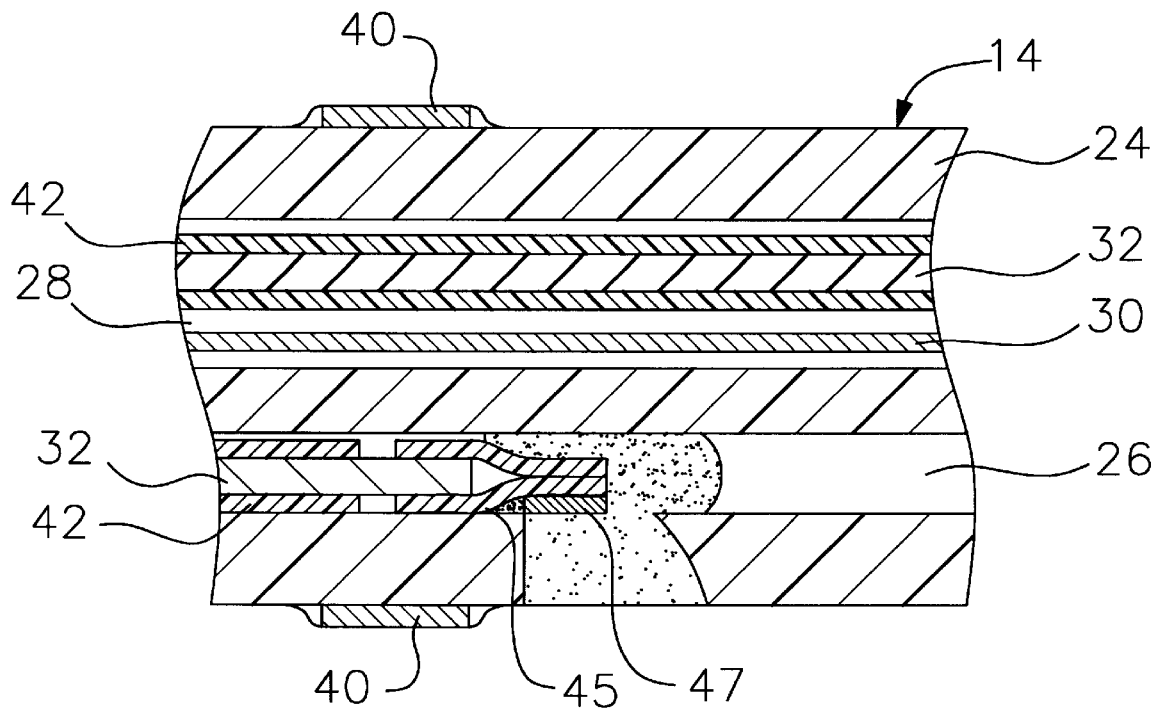
FIG. 6 is a transverse cross-sectional view of a catheter tip section according to the invention where the puller wires are anchored to the side walls of the tip section.
Figure 7:
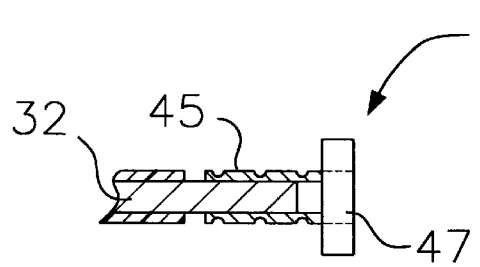
FIG. 7 is a longitudinal cross-sectional view of a preferred puller wire T-bar anchor.
Figure 8:
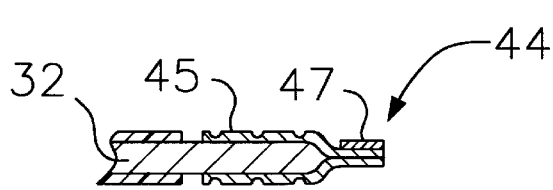
FIG. 8 is a longitudinal cross-sectional view of the puller wire T-bar anchor of FIG. 7 rotated 90° to show the cross-piece on end.

Alternatively, the puller wire 32 in the first off-axis lumen 26 can be anchored to the side wall of the tip section 14. As shown in FIGS. 6 to 8, the puller wire 32 is preferably attached by means of an anchor 44 fixedly attached to the distal end of the puller wire 32. The anchor 44 is formed by a metal tube 45, e.g., a short segment of hypodermic stock, that is fixedly attached, e.g. by crimping, to the distal end of the puller wire 32. The tube has a section that extends a short distance beyond the distal end of the puller wire 32. A cross-piece 47 made of a small section of stainless steel ribbon or the like is soldered or welded in a transverse arrangement to the distal end of the metal tube which is flattened during the operation. This creates a T-bar anchor 44. A notch is created in the side of the tip section 14 resulting in an opening in the off-axis lumen 26 carrying the puller wire 32. The cross piece 47 lies transversely within the notch. Because the length of the ribbon forming the cross-piece 47 is longer than the diameter of the opening into the off-axis lumen 26, the anchor 44 cannot be pulled completely into the off-axis lumen 26. The notch is then sealed with polyurethane glue or the like to give a smooth outer surface. The glue flows into the off-axis lumen 26 to fully secure the anchor. A tunnel, in the form of polyimide tubing or the like, can be provided to permit passage of the lead wire 30 through the glue so that this same puller wire anchor construction can be used in the second off-axis lumen 28. Other means for anchoring the puller wires 32 in the tip section 14 would be recognized by those skilled in the art and are included within the scope of the invention.

The catheter 10 further comprises two compression coils 46, each in surrounding relation to a corresponding puller wire 32. Each compression coil 46 is made of any suitable metal, such as stainless steel. Each compression coil 46 is tightly wound on itself to provide flexibility, i.e., bending, but to resist compression. The inner diameter of each compression coil 46 is slightly larger than the diameter of its associated puller wire 32. For example, when a puller wire 32 has a diameter of about 0.007 inch, the corresponding compression coil 46 preferably has an inner diameter of about 0.008 inch. The coating on the puller wires 32 allows them to slide freely within the compression coil 46. The outer surface of each compression coil 46 is covered along most of its length by a flexible, non-conductive sheath 48 to prevent contact between the compression coil 46 and the lead wires 30 within the central lumen 18. A non-conductive sheath 48 made of thin-walled polyimide tubing is presently preferred.

At the distal end of the catheter body, the two compression coils 46 are positioned in diametric opposition within the stiffening tube 22 and spacer 36 so that they can be aligned with the two off-axis lumens 26,28 in the tip section 14. The compression coils 46 and stiffening tube 22 are sized so that the compression coils 46 fit closely and slidably within the stiffening tube 22. With this design, the lead wires 30 distribute themselves around the two compression coils 46 without misaligning the coils.

The compression coils 46 are secured within the catheter body 12 with polyurethane glue or the like. Each compression coil 46 is anchored at its proximal end to the proximal end of the stiffening tube 22 in the catheter body 12 by a glue joint (not shown). When a stiffening tube 22 is not used, each compression coil is anchored directly to the outer wall 20 of the catheter body 12.

The distal end of each compression coil 46 is anchored to the distal end of the stiffening tube 22 in the catheter body 12 by a glue joint 52, or directly to the distal end of the outer wall 20 of the catheter body 12 when no stiffening tube 22 is used. Alternatively, the distal ends of the compression coils 46 may extend into the off-axis lumens 26,28 of the tip section 14 and are anchored at their distal ends to the proximal end of the tip section 14 by a glue joint. In the depicted embodiment, where the compression coils 46 are each surrounded by a sheath 48, care should be taken to insure that the sheath is reliably glued to the compression coil. The lead wires 30 can also be anchored in the glue joint. However, if desired, tunnels in the form of plastic tubing or the like can be provided around the lead wires at the glue joint to permit the lead wires to be slidable within the glue joint.

Both glue joints preferably comprise polyurethane glue or the like. The glue may be applied by means of a syringe or the like through a hole made between the outer surface of the catheter body 20 and the central lumen 18. Such a hole may be formed, for example, by a needle or the like that punctures the outer wall 18 and the stiffening tube 22 that is heated sufficiently to form a permanent hole. The glue is then introduced through the hole to the outer surface of the compression coil 46 and wicks around the outer circumference to form a glue joint about the entire circumference of each sheath 48 surrounding each compression coil 46. Care must be taken to insure that glue does not wick over the end of the coil so that the puller wire cannot slide within the coil.

Within the off-axis lumens 26, 28, each puller wire 32 is surrounded by a plastic sheath 42, preferably made of Teflon®. The plastic sheathes 42 prevent the puller wires 32 from cutting into the wall of the tip section 14 when the tip section is deflected. Each sheath 42 ends near the distal end of each puller wire 32. Alternatively, each puller wire 32 can be surrounded by a compression coil where the turns are expanded longitudinally, relative to the compression coils extending through the catheter body, such that the surrounding compression coil is both bendable and compressible.

Figure 9A:
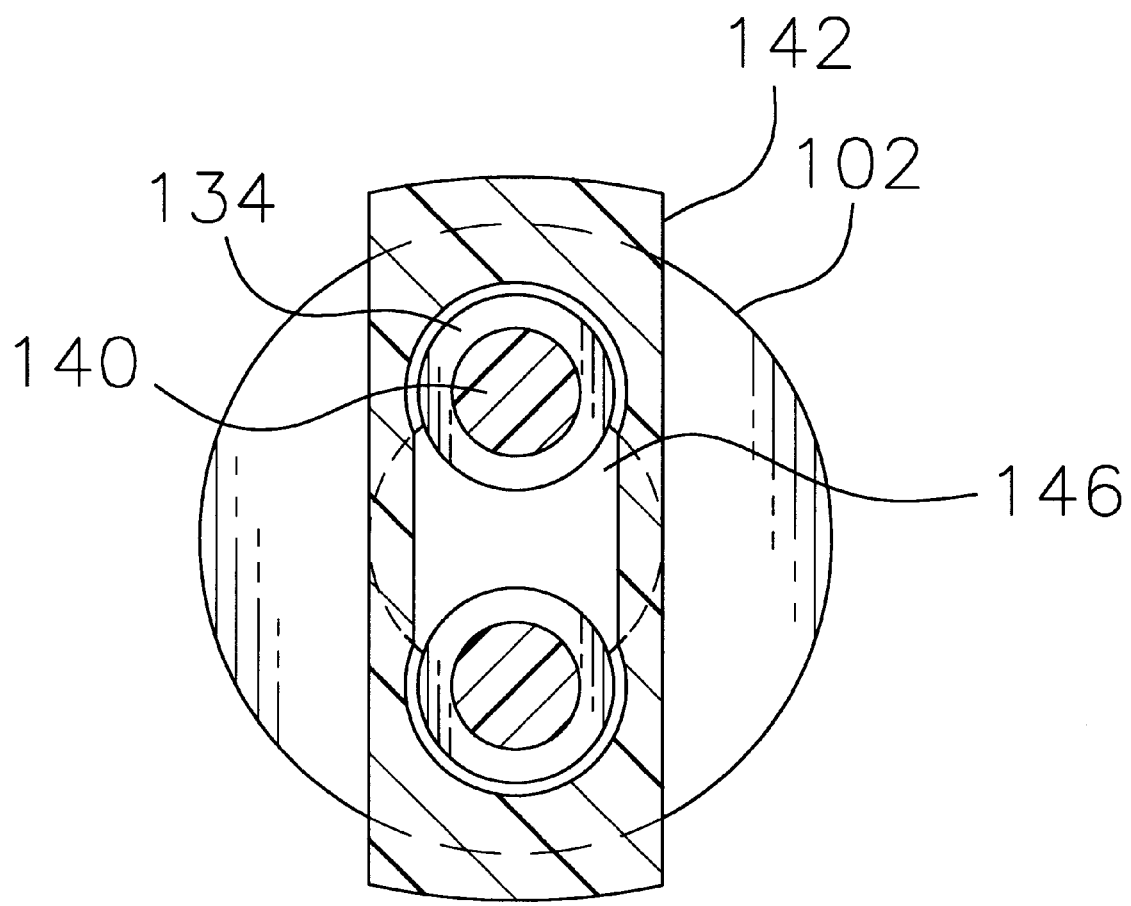
FIG. 9A is a longitudinal cross-sectional view of the bidirectional control handle of FIG. 9 along line 9A—9A.
Figure 9B:
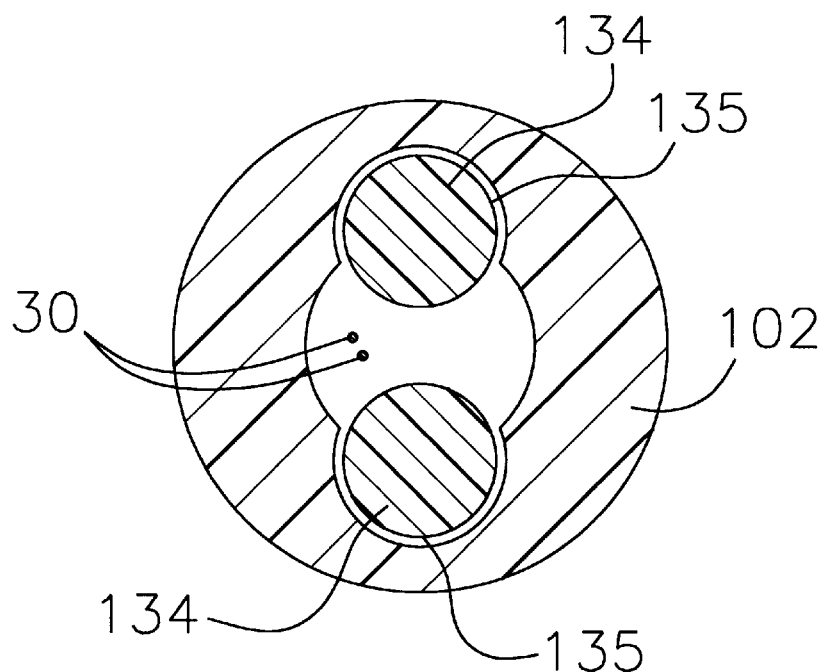
FIG. 9B is a longitudinal cross-sectional view of the bidirectional control handle of FIG. 9 along line 9B—9B.
Figure 9C:
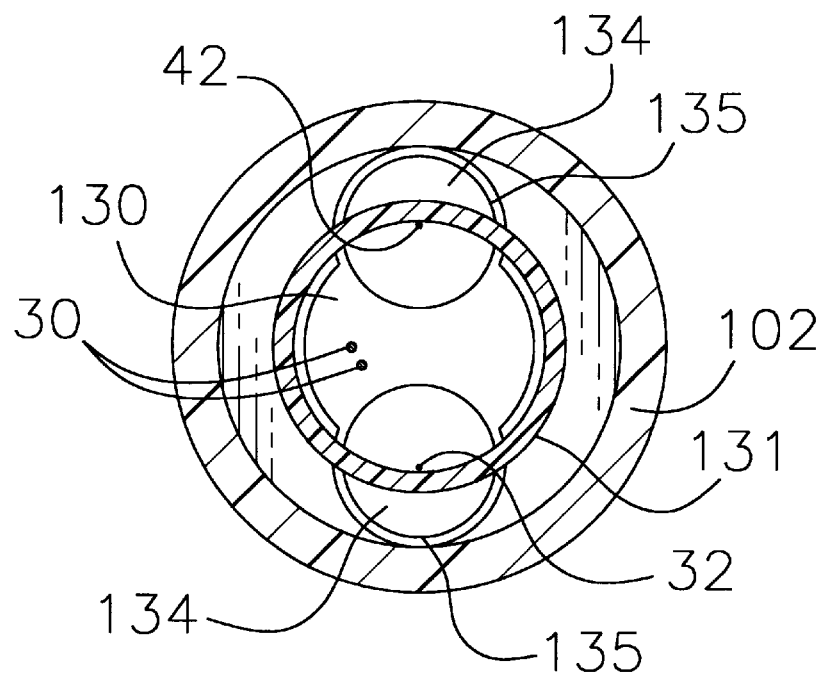
FIG. 9C is a longitudinal cross-sectional view of the bidirectional control handle of FIG. 9 along line 9C—9C.
Figure 10A:
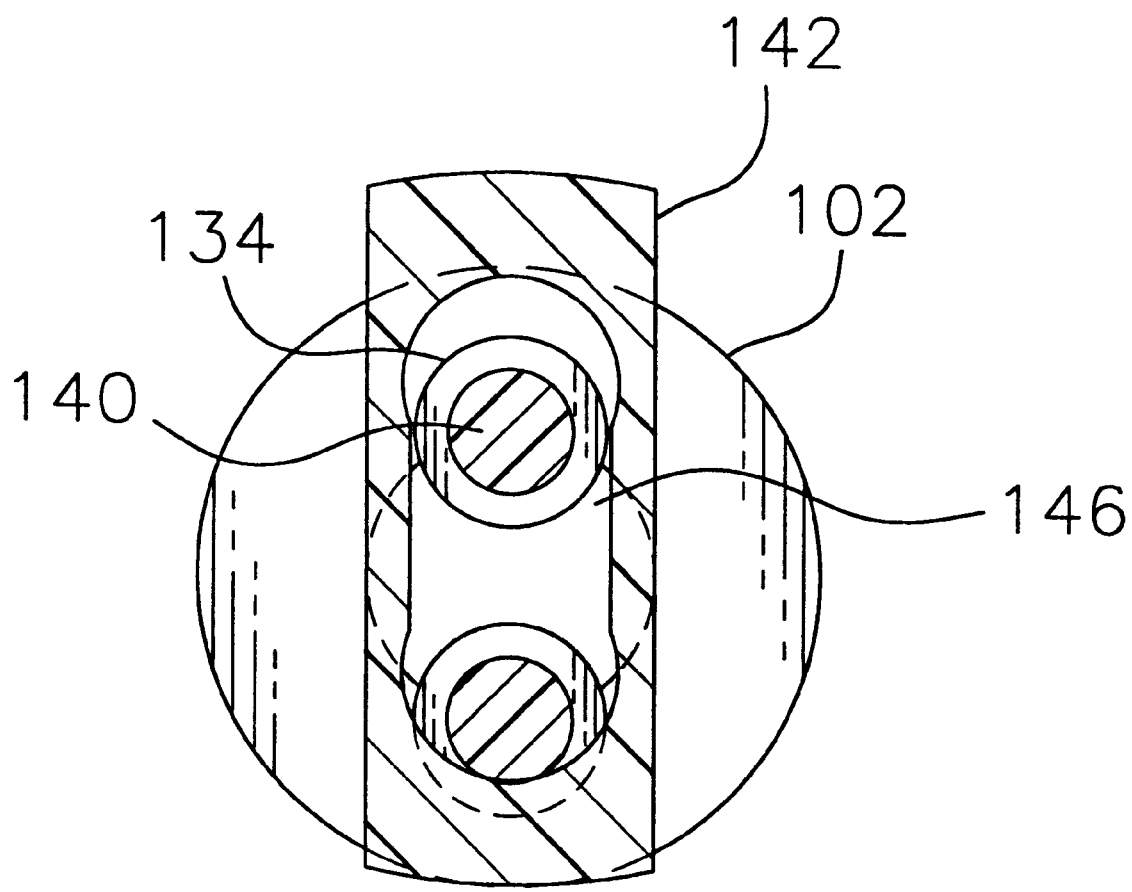
FIG. 10A is a longitudinal cross-sectional view of the bidirectional control handle of FIG. 10 along line 10A—10A.
Figure 11:
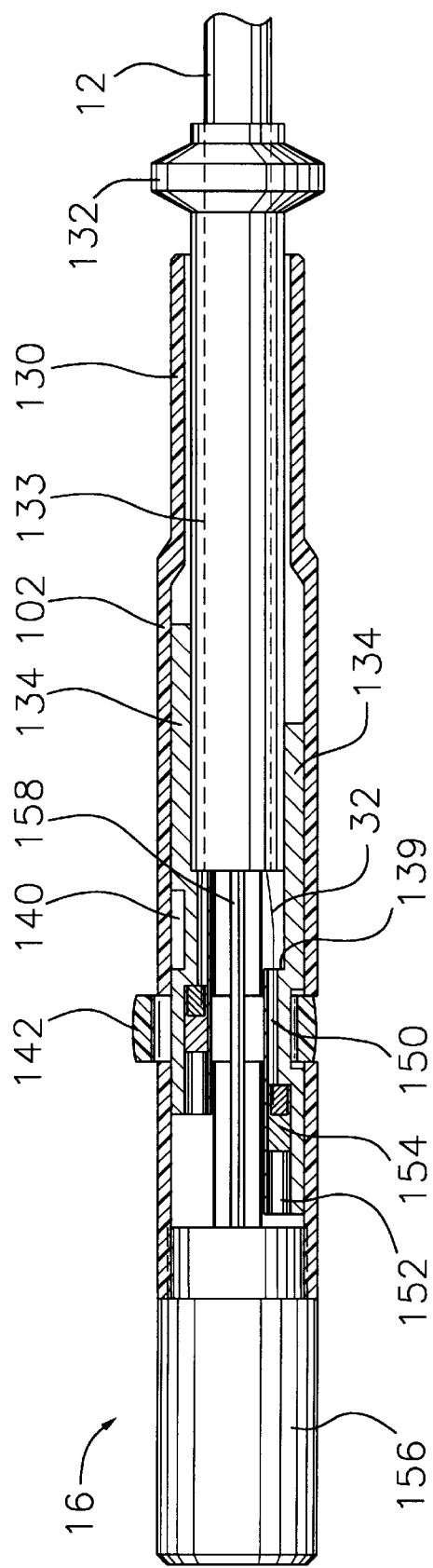
FIG. 11 is a side cross-sectional view of an alternative bidirectional control handle suitable for use with the invention.

Longitudinal movement of a puller wire 32 relative to the catheter body 12, which results in deflection of the tip section 14, is accomplished by suitable manipulation of the control handle 16. A suitable bidirectional control handle for use in the present invention is illustrated in FIGS. 9, 10 and 11. As shown in FIGS. 9, 9A, 9B and 9C, the control handle 16 comprises a generally tubular handle housing 102, which can be made of any suitable rigid material. The housing 102 comprises three piston chambers, an axial distal piston chamber 131 and two smaller proximal piston chambers 135. The proximal piston chambers 135 are preferably diametrically opposed in the housing and overlap the distal piston chamber 131. Mounted within the distal piston chamber 131 and extending out of the distal end of the housing 102 is a slidable distal piston 130 having a thumb rest 132 at its distal end and an axial passage 133. The proximal end of the catheter body 12 is attached, e.g., by glue, to the distal piston 130 in the axial passage 133. The puller wires 32 and lead wires 30 extend through the axial passage 133 of the distal piston 130. Proximal to the distal piston 130, two slidable proximal pistons 134 are located in the proximal piston chambers 135. The proximal pistons 134 can be made of any suitable material. Aluminum is presently preferred. Each puller wire 32 is anchored at its proximal end to the proximal piston 134 at some location along its length. The puller wires 32 can be fixedly attached to the proximal pistons 134 by any suitable means, for example, by means of a coupling as described above.

In this arrangement, distal movement of the distal piston 130 relative to the handle housing 102 by pushing on the thumb rest 132 also results in distal movement of the catheter body 12, the puller wires 32 and the proximal pistons 134 to which the puller wires are attached. Tip deflection does not occur however when both puller wires and their proximal pistons are allowed to move simultaneously. Accordingly, means are provided for preventing simultaneous movement of the proximal pistons 134.

The means for preventing simultaneous movement of the puller wires 32 comprises means for anchoring, i.e., preventing movement of one, but not both, of the proximal pistons 134. This is done by the combination of a circumferential notch 140 along the length of each proximal piston 134 and a means for engaging the circumferential notch 140 of a selected one of the proximal pistons 134.

A preferred engaging means comprises a movable bar 142 that extends diametrically through the handle housing 102 and extends slightly out of the housing on each side to thereby create what appears to be a button on each side of the housing at a position corresponding to the circumferential notches 140 of the proximal pistons 134 as shown in FIGS. 9 and 9A. As shown in FIGS. 10 and 10A, the bar 142 comprises a generally oval slot 146. Both of the proximal pistons 134 extend through the slot 146. The slot 146 has a width slightly greater than the diameter of the proximal pistons 134. The height of the bar 142 is less than the length of the circumferential notches 140 so that the bar 142 can be received by and engages the notches 140. The length of the slot 146 is selected to allow lengthwise movement of only one proximal piston 134 at a time. That is, as shown in FIG. 10, the bar 142 has been moved in a first direction until the end of the slot 146 engages the circumferential notch of one proximal piston 134. In this arrangement, the engaged proximal piston is prevented from moving longitudinally by the bar 142, but the other proximal piston can move freely through the slot 146. If the bar 142 is moved in the other direction the previously engaged proximal piston will be afforded free longitudinal movement and the previously freely moving proximal piston will be engaged.

When a proximal piston 134 is engaged by the bar 142, it acts as a fixed anchor for the puller wire 32 attached to it. Hence when the distal piston 130 is moved distally relative to the housing 102 by pushing the thumb rest 132, the catheter body 12 will move distally relative to the anchored puller wire 32. This results in deflection of the tip section 14 in the direction of the tip lumen carrying that puller wire. When the opposite proximal piston is engaged, deflection of the tip in the opposite direction will occur.

Another alternative bidirectional control handle is shown in FIG. 11. The handle 16 is similar to that depicted in FIGS. 9 and 10, but the proximal pistons 134 are not generally cylindrical. Instead, each proximal piston 134 has a distal portion comprising a generally semicircular transverse cross section, with the flat side of the semicircular distal portion facing toward the center of the handle 16. The proximal portion of each proximal piston 134 is generally cylindrical, creating a step 139 at the junction of the distal and proximal portions of the proximal pistons. Each of the proximal pistons 134 also has a notch 140, like the proximal piston described in the embodiment discussed above. Each proximal piston 134 receives a corresponding puller wire 32 through a small bore 150 at step 139 which extends proximally a select distance. At the proximal end of each proximal piston 134 is a larger distal bore 152, which extends distally into communication with the small bore 150. The proximal end of each puller wire 32 comprises an anchor 154, which slidably fits within the larger distal bore 152, but is too large to pass into the small bore 150. The anchor 154 can be formed, for example, by soldering the proximal end of the puller wire 32 to hypodermic stock or the like.

In the embodiment depicted in FIG. 11, the proximal end of the control handle 16 comprises a plug 156. The distal end of the plug 156 is threaded to correspond to threading in the proximal end of the handle body 102. Extending distally from the plug 156 is a protective tube 158, preferably made of metal, through which the lead wires 30 and any other cables, wires or the like that extend through the axial passage 133 in the distal piston 130 can pass. The plug 156 can contain a suitable connector (not shown) to facilitate an electrical connection between, for example, the lead wires 30 and an appropriate monitor and/or RF energy source.

Any other suitable bidirectional control handle can be used in connection with the present invention. Such handles are described, for example, in U.S. patent application Ser. Nos. 08/924,611, 09/143,426 and 09/130,359, and U.S. Pat. Nos. 6,123,699 and 6,120,476 the disclosures of which are incorporated herein by reference.

In other embodiments, one or more additional off axis lumens may be provided through which additional components, e.g., infusion tube, optic fiber, etc., may extend. Depending on the intended use of the catheter 10, it can further comprise additional features such as temperature sensing means, an optic fiber, an infusion tube, and/or an electromagnetic sensor. Additionally, smaller components, such as a temperature sensing means, could also extend through the second lumen in the tip section along with the puller wire and lead wire(s).

In the embodiments described above, the central lumen 18 of the catheter body 12 is used for passage of the electrode lead wires 30 as well as the two puller wires 32, compression coils 46 and, if present, thermocouple wires, electromagnetic sensor cable, optic fiber or infusion tube. It is understood that the catheter body 12 could alternatively comprise a plurality of lumens. However, the single central lumen 18 is preferred because it has been found that a single lumen body permits better control when rotating the catheter 10. The single central lumen 18 permits the puller wires 32, compression coils 46 and lead wires 30 to float freely within the catheter body 12. If such wires are restricted within multiple lumens, they tend to build up energy when the control handle 16 is rotated, resulting in the catheter body 12 having a tendency to rotate back if, for example, the handle 16 is released, or if bent around a curve, to flip over, either of which are undesirable performance characteristics.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A bi-directional catheter comprising:

an elongated catheter body having proximal and distal ends and at least one lumen therethrough;

a catheter tip section at the distal end of the catheter body comprising a flexible tubing having proximal and distal ends and first and second diametrically-opposed off-axis lumens, wherein the first off-axis lumen is smaller than the second off-axis lumen, and wherein the diameter of the tip section is no greater than 6½ French;

a control handle at the proximal end of the catheter body, the control handle comprising at least two moveable members longitudinally movable between first and second positions;

first and second puller wires, each puller wire having proximal and distal ends, the proximal end of each puller wire being connected to an associated movable member of the control handle, and each puller wire extending from the control handle through a lumen of the catheter body, wherein the first puller wire extends into the first lumen in the tip section and the second puller wire extends into the second lumen in the tip section, and wherein the distal end of each puller wire is anchored to the tip section;

an electrode mounted on the tip section;

a lead wire having a distal end electrically connected to the electrode, the lead wire extending through the second lumen in the tip section, through a lumen in the catheter body and through the control handle;

wherein proximal movement of a movable member relative to the catheter body results in proximal movement of the puller wire associated with that movable member relative to the catheter body, and thus deflection of the tip section in the direction of the off-axis lumen in which that puller wire extends.

2. A bi-directional catheter as claimed in claim 1, further comprising two compression coils, each extending through the catheter body in surrounding relation to each puller wire and having proximal and distal ends, wherein the proximal end of each compression coil is fixedly secured near the proximal end of the catheter body and the distal end of each compression coil is fixedly secured near the distal end of the catheter body or the proximal end of the tip section.

3. A bi-directional catheter as claimed in claim 1, wherein the catheter body has a single lumen.

4. A bi-directional catheter as claimed in claim 1, wherein the tip section carries a tip electrode.

5. A bi-directional catheter as claimed in claim 1, wherein the tip section carries at least one ring electrode.

6. A bi-directional catheter as claimed in claim 1, wherein the tip section carries both a ring electrode and a tip electrode.

7. A bi-directional catheter as claimed in claim 1, wherein the diameter of the tip section is no greater than 7 French.

8. A bi-directional catheter as claimed in claim 1, wherein the first off-axis lumen has a diameter ranging from about 0.018 inch to about 0.025 inch.

9. A bi-directional catheter as claimed in claim 1, wherein the first off-axis lumen has a diameter ranging from about 0.018 inch to about 0.022 inch.

10. A bi-directional catheter as claimed in claim 1, wherein the second off-axis lumen has a diameter ranging from about 0.022 inch to about 0.030 inch.

11. A bi-directional catheter as claimed in claim 1, wherein the second off-axis lumen has a diameter ranging from about 0.026 inch to about 0.028 inch.

12. A bi-directional catheter as claimed in claim 1, wherein the first off-axis lumen has a diameter ranging from about 0.018 inch to about 0.025 inch and the second off-axis lumen has a diameter ranging from about 0.022 inch to about 0.030 inch.

13. A bi-directional catheter as claimed in claim 1, wherein the first off-axis lumen has a diameter ranging from about 0.018 inch to about 0.022 inch and the second off-axis lumen has a diameter ranging from about 0.026 inch to about 0.028 inch.

14. A bi-directional catheter as claimed in claim 1, wherein the flexible tubing of the tip section comprises stainless steel braiding.

15. A bi-directional catheter comprising:

an elongated catheter body having proximal and distal ends and at least one lumen therethrough;

a catheter tip section at the distal end of the catheter body comprising a flexible tubing having proximal and distal ends and consisting essentially of first and second diametrically-opposed off-axis lumens;

a control handle at the proximal end of the catheter body, the control handle comprising at least two moveable members longitudinally movable between first and second positions;

first and second puller wires, each puller wire having proximal and distal ends, the proximal end of each puller wire being connected to an associated movable member of the control handle, and each puller wire extending from the control handle through a lumen of the catheter body, wherein the first puller wire extends into the first lumen in the tip section and the second puller wire extends into the second lumen in the tip section, and wherein the distal end of each puller wire is anchored to the tip section;

an electrode mounted on the tip section;

a lead wire having a distal end electrically connected to the electrode, the lead wire extending through the second lumen in the tip section, through a lumen in the catheter body and through the control handle;

wherein proximal movement of a movable member relative to the catheter body results in proximal movement of the puller wire associated with that movable member relative to the catheter body, and thus deflection of the tip section in the direction of the off-axis lumen in which that puller wire extends.

16. A bi-directional catheter as claimed in claim 15, wherein the flexible tubing of the tip section comprises stainless steel braiding.

17. A bi-directional catheter as claimed in claim 15, wherein the first off-axis lumen is smaller than the second off-axis lumen.

18. A bi-directional catheter as claimed in claim 15, wherein the diameter of the tip section is no greater than 7 French.

19. A bi-directional catheter as claimed in claim 15, wherein the diameter of the tip section is no greater than 6½ French.

20. A bi-directional catheter as claimed in claim 15, wherein the first off-axis lumen has a diameter ranging from about 0.018 inch to about 0.025 inch.

21. A bi-directional catheter as claimed in claim 15, wherein the first off-axis lumen has a diameter ranging from about 0.018 inch to about 0.022 inch.

22. A bi-directional catheter as claimed in claim 15, wherein the second off-axis lumen has a diameter ranging from about 0.022 inch to about 0.030 inch.

23. A bi-directional catheter as claimed in claim 15, wherein the second off-axis lumen has a diameter ranging from about 0.026 inch to about 0.028 inch.

24. A bi-directional catheter as claimed in claim 15, wherein the first off-axis lumen has a diameter ranging from about 0.018 inch to about 0.025 inch and the second off-axis lumen has a diameter ranging from about 0.022 inch to about 0.030 inch.

25. A bi-directional catheter as claimed in claim 15, wherein the first off-axis lumen has a diameter ranging from about 0.018 inch to about 0.022 inch and the second off-axis lumen has a diameter ranging from about 0.026 inch to about 0.028 inch.

26. A bi-directional catheter comprising:

an elongated catheter body having proximal and distal ends and at least one lumen therethrough;

a catheter tip section at the distal end of the catheter body comprising a flexible tubing having proximal and distal ends and first and second diametrically-opposed off-axis lumens, wherein the first off-axis lumen has a diameter ranging from about 0.018 inch to about 0.025 inch, and wherein the first off-axis lumen is smaller than the second off-axis lumen;

a control handle at the proximal end of the catheter body, the control handle comprising at least two moveable members longitudinally movable between first and second positions;

first and second puller wires, each puller wire having proximal and distal ends, the proximal end of each puller wire being connected to an associated movable member of the control handle, and each puller wire extending from the control handle through a lumen of the catheter body, wherein the first puller wire extends into the first lumen in the tip section and the second puller wire extends into the second lumen in the tip section, and wherein the distal end of each puller wire is anchored to the tip section;

an electrode mounted on the tip section;

a lead wire having a distal end electrically connected to the electrode, the lead wire extending through the second lumen in the tip section, through a lumen in the catheter body and through the control handle;

wherein proximal movement of a movable member relative to the catheter body results in proximal movement of the puller wire associated with that movable member relative to the catheter body, and thus deflection of the tip section in the direction of the off-axis lumen in which that puller wire extends.

27. A bi-directional catheter comprising:

an elongated catheter body having proximal and distal ends and at least one lumen therethrough;

a catheter tip section at the distal end of the catheter body comprising a flexible tubing having proximal and distal ends and first and second diametrically-opposed off-axis lumens, wherein the second off-axis lumen has a diameter ranging from about 0.022 inch to about 0.030 inch, and wherein the first off-axis lumen is smaller than the second off-axis lumen;

a control handle at the proximal end of the catheter body, the control handle comprising at least two moveable members longitudinally movable between first and second positions;

first and second puller wires, each puller wire having proximal and distal ends, the proximal end of each puller wire being connected to an associated movable member of the control handle, and each puller wire extending from the control handle through a lumen of the catheter body, wherein the first puller wire extends into the first lumen in the tip section and the second puller wire extends into the second lumen in the tip section, and wherein the distal end of each puller wire is anchored to the tip section;

an electrode mounted on the tip section;

a lead wire having a distal end electrically connected to the electrode, the lead wire extending through the second lumen in the tip section, through a lumen in the catheter body and through the control handle;

wherein proximal movement of a movable member relative to the catheter body results in proximal movement of the puller wire associated with that movable member relative to the catheter body, and thus deflection of the tip section in the direction of the off-axis lumen in which that puller wire extends.

* * * * *